United States Patent
Xiao et al.

(10) Patent No.: US 11,155,569 B2
(45) Date of Patent: Oct. 26, 2021

(54) METHOD OF DEGRADING POLYSACCHARIDE USING OZONE

(71) Applicant: GREEN VALLEY (SHANGHAI) PHARMACEUTICALS CO., LTD., Shanghai (CN)

(72) Inventors: Zhongping Xiao, Shanghai (CN); Zhenqing Zhang, Suzhou (CN); Meiyu Geng, Shanghai (CN); Jian Ding, Shanghai (CN)

(73) Assignee: GREEN VALLEY (SHANGHAI) PHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/474,350

(22) PCT Filed: Dec. 27, 2017

(86) PCT No.: PCT/CN2017/118897
§ 371 (c)(1),
(2) Date: Jun. 27, 2019

(87) PCT Pub. No.: WO2018/121581
PCT Pub. Date: Jul. 5, 2018

(65) Prior Publication Data
US 2019/0345184 A1 Nov. 14, 2019

(30) Foreign Application Priority Data
Dec. 30, 2016 (WO) ................ PCT/CN2016/113881

(51) Int. Cl.
*C07H 1/08* (2006.01)
(52) U.S. Cl.
CPC .................... *C07H 1/08* (2013.01)
(58) Field of Classification Search
CPC .................... C07H 1/00; C07H 1/08
See application file for complete search history.

(56) References Cited

FOREIGN PATENT DOCUMENTS

| CN | 101240040 A | 8/2008 |
|---|---|---|
| CN | 102875696 A | 1/2013 |
| CN | 202945189 U | 5/2013 |
| CN | 105624022 A | 6/2016 |
| CN | 106146682 A | 11/2016 |
| JP | S50-16789 A | 2/1975 |
| JP | S624703 A | 1/1987 |
| JP | 2016-108474 A | 6/2016 |
| WO | 1994/29510 A1 | 12/1994 |

OTHER PUBLICATIONS

Li, X. et al., Carbohydrate Polymers, "Preparation of low molecular weight alginate by hydrogen peroxide depolymerization for tissue engineering", 2010, vol. 79, pp. 660-664 (Year: 2010).*
Prajapat, A. L. et al., Ultrasonics Sonochemistry, Jan. 2016, vol. 31, pp. 371-382 (Year: 2016).*
Xu, X. et al., Current Topics in Medicinal Chemistry, "Characterization and Immunological Evaluation of Low-Molecular-Weight Alginate Derivatives", 2016 (publically available in 2015), vol. 16, pp. 874-887 (Year: 2015).*
Zhao, X. et al., Carbohydrate Polymers, "Preparation of low-molecular-weight polyguluronate sulfate and its anticoagulant and anti-inflammatory activites", 2007, vol. 69, pp. 272-279 (Year: 2007).*
Masuko, S. et al., Carbohydrate Research, "Ozonolysis of the double bond of the unsaturated uronate residue in low-molecular-weight heparin and K5 heparosan", 2011, vol. 346, pp. 1962-1966 (Year: 2011).*
International Search Report and Written Opinion for Application No. PCT/CN2017/118897, dated Apr. 2, 2018, 9 pages.
Katai et al., Mechanism of ozone attack on alpha-methyl glucose and cellulosic materials. J Polym Sci. Jan. 1966;4:2683-703.
Wang et al., Ozonolytic depolymerization of polysaccharides in aqueous solution. Carbohydr Res. Jun. 1999;319 (1-4):141-7.
Akhlaq et al., Degradation of the Polysaccharide Alginic Acid: A Comparison of the Effects of UV light and Ozone. Environ Sci Technol. 1990;24:379-383.
Duan et al., Oxidative depolymerization of polysaccharides by reactive oxygen/nitrogen species. Glycobiology. Apr. 2011;21(4):401-9.
Lou et al., Degradation of Konjac Glucomannan with Ozone. Science and Technology of Food Industry. 2009;30 (20):203-206.
Masuko et al., Ozonolysis of the double bond of the unsaturated uronate residue in low-molecular-weight heparin and K5 heparosan. Carbohydr Res. Sep. 27, 2011;346(13):1962-6.
Tang et al., Preparation of chito-oligosaccharide by ozone degradation Science and Technology of Food Industry. 2012;33(10):250-256.
Xu, Seaweed Chemistry and Technology. Ocean University of China Press. pp. 39-40, Sep. 30, 2014.

(Continued)

*Primary Examiner* — Bahar Craigo
(74) *Attorney, Agent, or Firm* — McCarter & English, LLP; Wei Song; Christopher D. Bayne (57) ABSTRACT

The present invention relates to a method for degrading a polysaccharide in the field of food, medicine or chemical industry. In particular, a molecular chain of the polysaccharide is broken by ozone into polysaccharides with smaller molecular weights, oligoses and/or oligosaccharides. The polysaccharides include linear or branched glycans extracted from plants, traditional Chinese medicinal materials, animals, fungi, or microorganisms and sulfated polysaccharides or esterified polysaccharides formed by sulfation or esterification thereof. As an oxidizing agent in the reaction, the ozone can be used alone or can be used under the catalysis of a base, a metal ion, hydrogen peroxide, UV light, or activated carbon to accelerate the reaction. The method for degrading the polysaccharide in the present invention uses milder reaction conditions compared to a conventional acid-catalytic degradation method, has higher reaction efficiency and a controllable reaction process, does not need to use an acid, and reduces environmental pollution.

18 Claims, 1 Drawing Sheet

(56) References Cited

OTHER PUBLICATIONS

Zhao et al., Effect of molecular weight on the antioxidant property of low molecular weight alginate from Laminaria iaponica. J Appl Phycol. 2012;24:295-300.

Chinese Office Action for Application No. 201711482873.0, dated Sep. 17, 2020, 9 pages.

Song et al., A comparative study of pre-ozonation and in-situ ozonation on mitigation of ceramic UF membrane fouling caused by alginate Journal of Membrane Science. Sep. 15, 2017;538:50-57.

European Office Action for Application No. 17886343.7, dated Jun. 17, 2021, 4 pages.

\* cited by examiner

METHOD OF DEGRADING POLYSACCHARIDE USING OZONE

CROSS-REFERENCE TO RELATED APPLICATIONS

This application is a U.S. national stage filing, under 35 U.S.C. § 371(c), of International Application No. PCT/CN2017/118897, filed on Dec. 27, 2017, which claims priority to International Application No. PCT/CN2016/113881, filed on Dec. 30, 2016. The entire contents of each of the aforementioned applications are incorporated herein by reference.

TECHNICAL FIELD

The present invention relates to degradation of polysaccharides in the fields of food, medicine and chemical industry, in particular to oxidative degradation of polysaccharides in the presence of ozone to generate polysaccharides with smaller molecular weights, oligoses or oligosaccharides. The method of the present invention is applicable to both naturally extracted polysaccharides and chemically modified polysaccharides, including sulfated polysaccharides, phosphorylated polysaccharides, formylated polysaccharides or acetylated polysaccharides.

BACKGROUND OF THE INVENTION

Like proteins, nucleic acids and fats, polysaccharides are basic substances that make up an organism. Polysaccharides are one of the structural substances of plant and microbial cell walls and animal carapace, for example, cellulose in plant cell walls, algal polysaccharides in algal cell walls, and N-acetylaminodextran in microbial cell walls. A large number of active polysaccharides are present in animal cells and body fluids, the most common being glycosaminoglycans. These polysaccharides are polymers formed of monosaccharide molecules bonded by glycosidic bonds, which may be linear, branched or reticular in shape. Polysaccharides are often associated with amino acids, fats, or the like in vivo, forming glycoproteins and glycolipids to exert various biological functions.

Naturally extracted polysaccharides have been widely used in food, medicine, and daily chemical industries, for example, starches in foods, *Lentinus edodes* polysaccharides and *Ganoderma lucidum* polysaccharides in health care products, the anticoagulant heparin, the thickening agent sodium alginate in jelly and toothpaste, etc. Naturally derived polysaccharides can be chemically modified to change their physicochemical properties. For example, acidic alginic acid has significantly improved water solubility under acidic conditions upon sulfation, and has lower water solubility and considerably increased viscosity upon formation of acetylated alginic acid with acetic acid. By chemical modification, the pharmacological activity of the polysaccharide also changes. For example, polyguluronic acid is sulfated to form a sulfated polyguluronic acid having an anti-tumor activity. In addition, degradation of a polysaccharide is also a commonly used polysaccharide modification strategy; that is, a polysaccharide having a large molecular weight is degraded into a polysaccharide having a low molecular weight or an oligosaccharide, thereby lowering the viscosity of the polysaccharide or improving its pharmacological activity in vivo. An example of the former is oligochitosan, and an example of the latter is low molecular weight heparin.

The most commonly used method for degrading polysaccharides is acid degradation. That is, under a heating condition, glycosidic bonds are hydrolyzed in acid water, and the sugar chain is broken. The method of acid hydrolysis is not suitable for all polysaccharides. For example, acid hydrolysis cannot be used in the production process for preparing low molecular weight heparin from heparin, because the structure of heparin contains sulfate, which can be easily destroyed in the case of direct acidolysis in water. The existing production processes for preparing low molecular weight heparin include nitrous acid, beta-elimination and hydrogen peroxide degradation methods. In addition, degradation of heparin by heparinase, periodic acid and hypochlorous acid have been reported.

Ozone can be used as a strong oxidizing agent for complete oxidative degradation of an organic matter to remove the organic matter. For example, ozone is widely used in sewage treatment, and is particularly suitable for treating sewage containing aromatic ring compounds and unsaturated double bond olefin compounds. See, for example, CN1182047C and CN1135117C. In addition, ozone is also used for disinfection and sterilization of foods, medical devices, drug products and the environment. In order to improve the sewage treatment capacity and the sterilization and disinfection effects of ozone, the ozone oxidation process employed in the industry is carried out in the presence of a catalyst, for example, as described in CN104310534B, CN1275883C, CN102151567B, CN102897895B, CN104192981B, etc. However, use of ozone in controllable degradation of polysaccharides has not been reported.

As described above, the most common process for polysaccharide degradation is acid degradation. This process requires a greater amount of an acid to be consumed. The reaction process often requires a high temperature and a high pressure to promote the reaction. After the reaction is completed, it is necessary to add a large amount of a base for neutralization. A large amount of salts will be generated during the production process, resulting in relatively difficult sewage treatment. Acid degradation is not suitable for acid-sensitive polysaccharides such as heparin. In the existing methods, the enzymolysis method has strong specificity, but has low reaction efficiency and high cost, and thus is not suitable for industrial large-scale production. As for the hydrogen peroxide degradation process, hydrogen peroxide is unstable at a high concentration, and puts forward a high requirement for storage conditions. Excess hydrogen peroxide needs to be removed by adding an excess of a base or sodium thiosulfate. The periodic acid or hypochlorous acid degradation process will produce considerable halogen element contamination. The nitrous acid method and the beta-elimination method are only suitable for polysaccharides having specific structures, have a narrow application range, and result in considerable environmental pollution and high production cost.

SUMMARY OF THE INVENTION

The present invention provides a production process for producing low molecular weight polysaccharides or oligosaccharides on the basis of degradation of a polysaccharide by ozone, and thus provides an important novel process over the existing production technology systems for degrading polysaccharides. The process greatly reduces the amount of an acid or base used. The reaction process is controllable and high in efficiency, and is particularly suitable for degradation of sulfated polysaccharides that have high water solubility, thereby avoiding loss of sulfate.

One aspect of the present invention relates to a method of controllable degradation of a water-soluble polysaccharide, characterized in that an aqueous solution of the polysaccharide is brought into contact with ozone, such that a sugar chain of the polysaccharide is subjected to an oxidative degradation reaction. The present inventors have found that by controlling the reaction conditions and the flux of ozone generation, the oxidation reaction of the polysaccharide can be carried out efficiently and controllably, and degraded polysaccharides having a desired range of molecular weights or even oligosaccharides can be obtained in a high yield. The present invention is particularly suitable for obtaining degraded polysaccharides having molecular weights in the range of 1-100 KDa.

The present invention offers the following advantages. 1) The novel process of degrading a polysaccharide using ozone has mild reaction conditions, without need of high temperature and high pressure reaction conditions as required for acid degradation. 2) The novel process allows for reacting under both acidic and alkaline conditions, and the polysaccharide that is insoluble under an acidic condition can react after being dissolved under an alkaline condition. 3) The novel process does not affect the acid- or base-sensitive groups in the sugar structure, and retains these key functional groups to the greatest extent, which is especially important for preparation of biologically active low molecular weight carbohydrate drugs. 4) An ozone source is readily available, and can be prepared by an industrial grade ozone generator in industrial production, which merely involves a simple operation. 5) Ozone will be automatically decomposed into oxygen, only transiently exists in the environment, and will not remain in the product. Unreacted ozone can be treated by an exhaust gas collecting device, without causing environmental pollution.

DETAILED DESCRIPTION OF THE INVENTION

Various aspects of the present invention will be described in detail below. However, the present invention is not limited to these specific embodiments. A person skilled in the art can make some modifications and adjustments to the present invention in light of the substantial disclosure below, and such modifications are also encompassed in the scope of the present invention.

The present invention relates to a method for oxidizing a polysaccharide using ozone as an oxidizing agent. Polysaccharides which can be used in the present invention include polysaccharides of natural origin extracted from plants, traditional Chinese medicinal materials, animals or microorganisms, and chemically modified products thereof, including, but not limited to:

1) polysaccharides extracted from plants and traditional Chinese medicinal materials, such as *Hericium erinaceus* polysaccharide, *Poria cocos* polysaccharide, *Tremella* polysaccharide, *Lentinus edodes* polysaccharide, *Ganoderma lucidum* polysaccharide, *Lycium barbarum* polysaccharide, *Astragalus* polysaccharide, algin, polymannuronic acid, and polyguluronic acid;

2) animal polysaccharides such as heparin, heparan sulfate, chondroitin sulfate, dermatan sulfate, hyaluronic acid, and chitosan;

3) polysaccharides extracted from microorganisms, such as xanthan gum; and 4) chemically modified products of the polysaccharides described in 1), 2) and 3) above, including sulfated polysaccharides, phosphorylated polysaccharides, formylated polysaccharides and acetylated polysaccharides.

In some embodiments of the present invention, raw materials of the polysaccharide are extracted from a traditional Chinese medicinal material, such as *Hericium erinaceus* polysaccharide, *Poria cocos* polysaccharide, *Tremella* polysaccharide, *Lentinus edodes* polysaccharide, *Ganoderma lucidum* polysaccharide, *Lycium barbarum* polysaccharide, *Astragalus* polysaccharide, and the like.

In other embodiments of the present invention, raw materials of the polysaccharide are commercially available, such as algin, heparin, heparan sulfate, chondroitin sulfate, dermatan sulfate, hyaluronic acid, chitosan, xanthan gum, and the like.

In still other embodiments of the present invention, polysaccharides that have undergone partial degradation can be obtained by known extraction techniques, such as polymannuronic acid (PM), polyguluronic acid (PG), sulfated polymannuronic acid (S-PM), and sulfated polyguluronic acid (S-PG).

Unless otherwise specified, the present invention extracts polysaccharides from traditional Chinese medicinal materials by the following steps. 1) The medicinal material is dried and then pulverized; and 5.0 Kg of the medicinal material powder is immersed in 50 L of distilled water for 12 hr. 2) The liquid is heated to reflux for 8 hr, cooled, and filtered through a filter cloth. 3) 100 L of ethanol (95%) is added to the filtrate for precipitation, and set aside for 12 hr. The supernatant is removed, and the precipitate is collected by centrifugation, vacuum dried under reduced pressure, pulverized, and weighed to obtain the polysaccharide product. The weights of the polysaccharides obtained by the exemplary extraction are shown in Examples 1-7.

The methods for preparing polymannuronic acid (PM) and polyguluronic acid (PG) can be briefly described as follows. Polymannuronic acid (PM) and polyguluronic acid (PG) are polymannuronic acid fragments and polyguluronic acid fragments, respectively, in sodium alginate molecules. They can be prepared by degrading sodium alginate followed by fractionation by acid precipitation to obtain polymannuronic acid (PM) and polyguluronic acid (PG), respectively. Exemplary extraction methods can be found in the patent CN100467492C. An exemplary extraction method can be found in Example 9.

The methods for preparing sulfated polymannuronic acid (S-PM) and sulfated polyguluronic acid (S-PG) can be briefly described as follows. The polymannuronic acid (PM) and polyguluronic acid (PG) powders obtained above are separately dispersed in pyridine, and allowed to be reacted with chlorosulfonic acid as a sulfonating agent. After the completion of the reaction, they are purified and dried to obtain sulfated polymannuronic acid (S-PM) and sulfated polyguluronic acid (S-PG), respectively. Exemplary extraction methods can be found in the patent CN1213071C. Exemplary extraction methods can also be found in Example 12 and Example 13.

In order to carry out a polysaccharide oxidation reaction, the polysaccharide is first dissolved in water, and optionally heated to promote the dissolution. The pH is adjusted to a desired range, and the solution is heated and stirred. An ozone generator is turned on, and the generated ozone is introduced into the reaction vessel, preferably accompanied by stirring. During the reaction, incompletely reacted ozone can be treated by an exhaust gas collecting device. After the completion of the reaction, the introduction of ozone is stopped. After the reaction solution is cooled down to room temperature, subsequent purification, concentration and drying steps are carried out.

The oxidation of a polysaccharide by ozone acts on the C—C bonds of the sugar ring or on the glycosidic bonds.

Applicant of the present invention has also discovered that ozone also has a ring opening effect on the end of the polysaccharide, which can oxidize the end of the polysaccharide to cause loss of one or more CH—OH structural units. Such a modification to the terminal structure of the polysaccharide can improve the biological activity of the degraded polysaccharide.

The concentration of the polysaccharide used for the oxidation reaction is usually 1-40%, preferably 4-30%, more preferably 8-25% in water. The concentration of the polysaccharide should not be too high. Too high concentrations can result in too large viscosity of the reaction system, which is not conducive to dispersion of the oxidizing agent. Additionally, the concentration of the polysaccharide should not be too low; otherwise, the efficiency of the oxidation reaction will be compromised. Applicant has found that the oxidation reaction can be smoothly performed when the concentration of the polysaccharide solution is 1-20%, and the viscosity is 1-10 mPa·s. The viscosity mentioned herein is determined by an Ubbelohde viscometer or a rotational viscometer; see, for example, the methods for measuring viscosity in the Chinese Pharmacopoeia.

Ozone can be supplied by an ozone generator. The ozone generator commonly used in the industry provides ozone by treating oxygen through high voltage discharging. The amount of ozone generated can be determined by measuring the ozone concentration at the outlet using an ozone concentration meter, taking into account the gas flow rate and the gas generation time. In the present invention, the ozone generation rate of the ozone generator is controlled to be between 1 g/hr and 10 g/hr by adjusting the operating power of the ozone generator and the outlet gas flow rate of the oxygen cylinder. For a pressurization reaction, the oxygen cylinder can provide a pressure in addition to the oxygen required for the preparation of ozone. The pressure of the reaction system in the present invention ranges from 0.1 MPa to 1.0 MPa. At normal temperature and pressure, about 1 g of pure ozone gas can be dissolved in 1 L of water. As the pressure is increased, the solubility of ozone will increase, thereby increasing the concentration of ozone in a solution, such that the collision probability between ozone and the reaction substrate is increased, and the reaction is accelerated. At normal temperature and pressure, the concentration of ozone in the solution can be measured by the iodometric method specified in the Chinese Standard GB/T5750.11-2006, "Standard Test Methods for Drinking Water". The ozone consumption amount in the present invention is 10-500 mg/g of polysaccharide based on the polysaccharide solid. Incompletely reacted ozone is sequentially introduced into exhaust gas collecting devices comprising sodium hydroxide and sodium thiosulfate. In some embodiments of the present invention, before the completion of the reaction, the concentration of ozone is maintained no more than 4 hours, preferably no more than 3 hours.

During the oxidation reaction, both heating and pH can affect the solubility of the polysaccharide and the reaction rate. Most polysaccharides have higher solubility in hot water than in cold water, and increasing the temperature can accelerate the reaction. In general, the temperature is maintained at about 20-60° C., preferably 20-50° C., during the reaction. For some weakly acidic carboxyl-containing polysaccharides, which are poorly soluble under acidic conditions, the pH can be adjusted to be alkaline. The pH of the reaction is usually maintained at 3-10. For carboxyl-containing polysaccharides, such as sodium alginate, polyguluronic acid, polymannuronic acid, etc., the pH can be adjusted to between 7 and 11, preferably between 8 and 10, more preferably 8-9.

In a preferred embodiment, the method of the present invention is carried out under an elevated pressure. The inventors have found that under an elevated reaction pressure and continuous agitation, when the ozone consumption amount is controlled to be 10-500 mg/g of polysaccharide based on the polysaccharide solid, an overall yield of greater than 80%, even greater than 90% or 95% or more, can be achieved, and the molecular weight distribution of the degradation product is uniform. Preferably, the reaction can be complete in about 4 hours, which can hardly be achieved by both the acid degradation method and the hydrogen peroxide degradation method. Without being bound by any theory, Applicant believes that the method of the present invention can achieve a very high polysaccharide yield by using an oxidizing agent with a strong oxidizing effect, and controlling the reaction pressure and reaction time, as well as the concentration of the solution, the amount of the oxidizing agent, and so on. The product has a uniform distribution and important industrial application values. The method can reduce production costs and environmental pollution.

More importantly, the oligosaccharides prepared by the method of the present invention show low or no toxicity to human or animal bodies and normal cells, and can be prepared into bioactive products with high-dose tolerance. For example, a mannuronic diacid oligosaccharide product is obtained in Example 17 according to the method of the present invention, which shows a significant biological activity of protecting nerve cells, and no toxicity can be detected.

In a more preferred embodiment, by using the method of the present invention, a biologically active degraded polysaccharide can be obtained in a high yield under the following conditions: the pressure in the oxidation reaction vessel is 0.1-1.0 MPa, and the concentration of the aqueous polysaccharide solution is 8-25%. The ozone consumption amount is controlled to be 100-300 mg/g of polysaccharide based on the polysaccharide solid. In particular, the method of the present invention is suitable for degradation of carboxyl-containing polysaccharides, such as sodium alginate, polyguluronic acid, polymannuronic acid, and the like. For polysaccharides extracted from natural medicinal materials, including, but not limited to, *Hericium erinaceus, Poria cocos, Tremella, Lentinus edodes, Ganoderma lucidum, Lycium barbarum, Astragalus*, etc., the present invention is particularly suitable for degrading them to a molecular weight of about 20-100 kDa, more preferably 20-80 kDa. For polysaccharides having relatively small molecular weights, they can be degraded into degradation products having a molecular weight of about 0.5-20 kDa. Moreover, regardless of the sources of the polysaccharides, the controllable degradation method of the present invention can achieve uniform degradation of the product, and the operation method is robust.

During the reaction, the degree of degradation of the polysaccharide is continuously monitored, and when the molecular weight of the polysaccharide is lowered to a desired range, the introduction of ozone is stopped. After the solution is cooled down to room temperature, subsequent treatments are carried out. Specifically, 1) the solution is directly concentrated and dried to obtain a solid product; or 2) a certain volume of 95% ethanol is added, such that the final volume concentration of ethanol reaches between 10% and 90%. The solution is allowed to stand to obtain a precipitate, and if necessary, it can be cooled to 4° C. in a cold storage to make the precipitation more complete, followed by separation to obtain the desired product. In addition, if necessary, the solution after the reaction can be charged into an ultrafiltration membrane concentration device, and concentrated by filtration using an ultrafiltration membrane having a desired molecular weight cut-off range. The membrane concentration process can remove part of undegraded polysaccharides or oligosaccharide fragments having too small molecular weights, yielding a polysaccharide degradation product with a moderate molecular weight and distribution.

The method of the present invention uses mild reaction conditions. For the polysaccharides which are not resistant to acids and bases, such as heparin, heparan sulfate, sulfated polyguluronic acid, etc., the reaction can be conducted under near-neutral and room temperature conditions, avoiding a decrease in biological activity due to loss of sulfate. The rate of generation of ozone free radicals can be accelerated by a base, a metal ion, hydrogen peroxide, ultraviolet light irradiation, etc., thereby accelerating the degradation reaction of the polysaccharide. A catalyst may be added at the beginning of the reaction or after the reaction has been conducted for a period of time. In a preferred embodiment, the catalyst is added when the oxidation reaction achieves about 50-80% of complete conversion, which can increase the degradation rate and degradation degree of the polysaccharide, and obtain an oligomeric oligosaccharide having a uniform size distribution (having a molecular weight of about 1-8 kDa, preferably 2-6 kDa, more preferably 2.5-5 kDa).

In an exemplary embodiment, the method of the present invention comprises the following steps:
(1) Preparation of a polysaccharide solution: The polysaccharide powder is weighed, and formulated in water to a concentration of 1-20%. Some polysaccharides need to be heated to promote dissolution, or adjusted to an alkaline pH by adding sodium hydroxide such that the polysaccharides can be completely dissolved. The solution is heated and stirred, and the temperature and pH are adjusted.
(2) Introduction of ozone and oxidative degradation reaction process: When the polysaccharide solution is prepared, an ozone generator is turned on, and the gas flow rate at the gas outlet of an oxygen cylinder and the discharge power of the ozone generator are adjusted, such that the concentration of ozone is about 10%. At this concentration by the discharging, ozone is produced at the best efficiency. The oxygen flow rate is adjusted in a range of from 1 L/min to 10 L/min, and the corresponding discharge power is between 10 W and 100 W. After the ozone generator stably supplies ozone, the ozone is introduced into the polysaccharide solution at the bottom, while the solution is continuously and rapidly stirred. A fine hole is created at the top of the sealed reaction vessel, and the exhaust gas is led to exhaust gas treatment devices.
(3) Treatment of polysaccharide degradation products: When the degradation reaction proceeds to a preset time point, the introduction of ozone is stopped, the heating device is removed, and the stirring is continued. After being cooled down to room temperature, 1) the polysaccharide degradation product is directly transferred to a concentration device, and oven-dried in vacuo after concentration; alternatively, 2) a certain volume of 95% ethanol is added such that the final concentration of ethanol is between 10% and 90%, and then alcohol precipitation, standing, obtaining a precipitate, centrifugation, and drying under reduced pressure are performed; alternatively, 3) the degradation product is filtered through a 0.22 μm ultrafiltration membrane, transferred to an ultrafiltration membrane device for concentration, further concentrated on a rotary evaporator, and dried under reduced pressure.

Analysis and Measurement Methods Used in the Present Invention

Measurement of Molecular Weight

The molecular weight of a polysaccharide is generally measured by a GPC gel-coupled Refractive Index Detector (RID) and/or a multi-angle laser light scattering (MALLS). In the examples of the present invention, GPC-RI-MALLS, i.e., GPC gel chromatography in combination with a Refractive Index Detector and a multi-angle laser scatterometer, is used to determine the molecular weights of various polysaccharides. For relevant technical details, please see Chinese patent CN101261203B. The specific procedure is described as follows:

100 mg of a dried polysaccharide sample is accurately weighed, dissolved in water to reach a concentration of 1 mg/mL, and passed through a 0.22 μm filter membrane to obtain a test sample solution. The molecular weight is measured by gel exclusion chromatography. The experimental conditions are as follows:

Chromatographic column: TSK3000
Mobile phase: 0.1 mol/L NaCl
Injection volume: 10 uL
Flow rate: 1 mL/min
Detectors: Refractive Index Detector, and 18-angle laser scatterometer Detection results and data processing: The chromatogram is processed by the instrument's own chromatogram processing software (ASTRA), and the molecular weight of the sample is calculated by the Zimm's extrapolation method.

Effect of Catalysts on Degradation Rate of Polysaccharides

In order to investigate the effect of catalysts on the rate of degradation of polysaccharides by ozone, changes in molecular weights of the polysaccharides with the degradation time are also monitored, the molecular weights of the samples taken at different time points in the presence of a catalyst are detected, and the degradation effects are compared to those observed when no catalyst is added. In the present invention, the following catalysts or reaction conditions are used to catalyze the ozone oxidation reaction: a base (hydroxide), a metal ion, hydrogen peroxide, activated carbon and ultraviolet light, wherein the metal ion includes iron ion and a soluble salt thereof, nickel ion and a soluble salt thereof, cobalt ion and a soluble salt thereof, and manganese ions (manganese dioxide). Exemplary operations can be found in Example 16 and FIG. 1.

Determination of Sulfate Content

The content of sulfate in sulfated polysaccharides is determined by ion chromatography as follows.

A standard series of solutions at concentrations of 1, 5, 10, 25, 50, and 100 ppm are prepared using a sulfate standard solution, and a standard curve is plotted. 10 mg of a sodium salt of polyguluronate sulfate polysaccharide is accurately weighed in duplicate. One aliquot is placed in a 5 mL volumetric flask, dissolved and made up to the mark with a suitable amount of deionized water, and shake well, to give a test solution for free sulfate determination. Another aliquot is placed in a 2 mL ampoule, 1 mL of 2 mol/L trifluoroacetic acid solution is added accurately, heat-sealed, and hydrolyzed at 120° C. for 3 h. 0.2 mL is taken accurately, and blow-dried with nitrogen at 90° C. The residue is dissolved in 1 mL of water, and centrifuged at a high speed. 0.25 mL of the supernatant is accurately pipetted into a 5 mL volumetric flask, made up to the mark with water, and shake well, to give a test solution for total sulfate determination. The standard solutions and the test solutions are separately injected into an ion chromatograph for analysis.

Chromatographic Conditions:

Chromatographic column: Metrosep A Supp 5-150/4.0 Column; column temperature: 30° C.; mobile phase: 3.2 mmol/L $Na_2CO_3$-1 mmol/L $NaHCO_3$ solution; inhibitor: 0.5% $H_2SO_4$ solution; flow rate: 0.7 mL/min; Injection volume: 10 μL.

Calculation of results: The calculation is performed on the basis of the dry product according to the following calculation formula:

$$SO_4^{2-}{}_{bound}(\%) = SO_4^{2-}{}_{total} - SO_4^{2-}{}_{free}$$

Advantages of the present invention are further illustrated in the following non-limiting examples. However, the specific materials and amounts thereof as well as other experimental conditions used in the examples should not be construed as limiting the present invention. The parts and percentages are both expressed by mass in the present invention, unless otherwise specified.

EXAMPLES

In the following examples, the data such as the weights of the polysaccharides extracted from plants and traditional Chinese medicinal materials, the degradation yields, and the molecular weights before and after degradation are listed in Table 1. The polysaccharide extraction process comprises extracting 1 part of traditional Chinese medicinal material in 10 parts of water under heating and refluxing, and drying and weighing the obtained polysaccharide. Degradation of the polysaccharide is carried out under an ozone condition, and the molecular weights before and after degradation are determined by the GPC-RI-MALLS method. The data such as the molecular weights and yields of the remaining polysaccharides before and after degradation are listed in Table 2.

Example 1

Step (1): Extraction of *Hericium erinaceus* polysaccharide. After the medicinal material was dried and pulverized, 5 kg was weighed into a 100 L reactor with a condensed water recovery device, immersed in 50 L of water for 12 hr, stirred, and heated. When the temperature was increased to 100° C., timing was started. At 8 hr of the extraction, the heating was stopped. The extract was discharged when cooled down to below 50° C. with cooling water, and filtered through a filter cloth. The filtrate was precipitated by adding 100 L of ethanol (95%), and allowed to stand for 12 hr. The supernatant was removed, and the precipitate was collected by centrifugation, vacuum dried under reduced pressure, pulverized and weighed to obtain 560 g of a polysaccharide product.

Step (2): Degradation of *Hericium erinaceus* polysaccharide. 400 g of the polysaccharide powder obtained above was weighed, mixed with 4 L of water, and heated to promote dissolution. It was placed for about 4 hr. When the temperature was adjusted back to 30° C., the outlet pressure of the oxygen cylinder was adjusted until the pressure of the reaction system was maintained at 0.8 MPa. The ozone generator was turned on, the output power was adjusted, and the ozone mass concentration was measured to be 0.5 g/L. The ozone was introduced into the reaction solution at the bottom, and the solution was stirred rapidly to make the solution sufficiently react with ozone. The exhaust gas was led to exhaust gas treatment devices through a pressure reducing valve at the top of the reaction device. The exhaust gas treatment devices are composed of a 6M NaOH solution and a 1 M sodium thiosulfate solution in series. The ozone was continuously supplied for 1 hr, then the introduction was stopped, and stirring was continued for 30 min.

Step (3): Treatment of degradation product of *Hericium erinaceus* polysaccharide: After the remaining ozone was absorbed, the reaction device was disassembled. The degraded polysaccharide solution was removed and transferred to a rotary evaporator for concentration under reduced pressure, and oven-dried in vacuo. After drying, it was pulverized and weighed to obtain 355.2 g of a polysaccharide degradation product.

Step (4): Determination of molecular weights of *Hericium erinaceus* polysaccharide before and after degradation: The molecular weights of the sample before and after degradation were measured as described above. The molecular weights of the sample calculated by the Zimm's extrapolation method were as below: the molecular weight of *Hericium erinaceus* polysaccharide was 650 KDa before degradation, and 60 KDa after degradation. The data such as the weights, molecular weights, and yields of *Hericium erinaceus* polysaccharide and the degradation product thereof are listed in Table 1.

Example 2

Step (1): 5.0 Kg of *Poria cocos* powder was weighed, and extracted by the same method as in Example 1 to give 610 g of polysaccharide powder.

The pressure in step (2) was set to 0.9 MPa, and other parameters were the same as in Example 1.

Steps (3) and (4) were the same as in Example 1. 365.2 g of degraded *Poria cocos* polysaccharide was obtained after degradation. The molecular weights before and after degradation were determined to be 740 KDa and 77 KDa, respectively. The results are shown in Table 1.

Example 3

Step (1): 5.0 Kg of *Tremella* powder was weighed, and extracted by the same method as in Example 1 to give 720 g of polysaccharide powder.

Step (2): the pressure was set to 0.2 MPa, the degradation time was 3 hr, and other parameters were the same as in Example 1.

Step (3): It was different from that of Example 1 in that the sample treatment after the reaction was ethanol precipitation. Specifically, 2 volumes of 95% ethanol were added to the filtrate, stirred to make the precipitate uniform, and placed in a cold storage at 4° C. overnight. Thereafter, the supernatant was aspirated, the lower layer was centrifuged, and the precipitate was collected, dried in an oven, pulverized and weighed to be 293.2 g.

Step (4) was the same as in Example 1. The molecular weights before and after degradation were determined to be 530 KDa and 46 KDa, respectively. The results are shown in Table 1.

Example 4

The extraction, degradation reaction, product treatment and molecular weight measurement of *Lentinus edodes* polysaccharide were the same as in Example 3. The results are shown in Table 1.

Example 5

Step (1): The extraction step for *Ganoderma lucidum* polysaccharide was the same as in Examples 3 and 4.

Step (2): The pressure was set to normal pressure, i.e., 0.1 MPa, the degradation time was 4 hr, and other parameters were the same as in Examples 3 and 4.

Step (3): It was different from that of Examples 3 and 4 in that the sample treatment after the reaction was concentration via an ultrafiltration membrane. Specifically, the reaction solution was filtered through a 0.22 μm filter membrane, and then filtered through an ultrafiltration membrane having a molecular weight cut-off of 20 KDa to collect a retentate. The collected liquid was concentrated on a rotary evaporator and dried in vacuo to yield 274.0 g.

Step (4) was the same as that of Examples 3 and 4. The molecular weights before and after degradation were measured, respectively. The molecular weight of the polysaccharide was greater than 1,000 KDa before degradation and was 22 KDa after degradation. The results are shown in Table 1.

Example 6

The extraction, degradation reaction, product treatment and molecular weight measurement of *Lycium barbarum* polysaccharide were the same as in Example 5. The results are shown in Table 1.

Example 7

Step (1): The extraction step for *Astragalus* polysaccharide was the same as in Examples 5 and 6.

Step (2): It was different from that of Examples 5 and 6 in that the degradation time was 3.5 hr.

Step (3): It was different from that of Examples 5 and 6 in that the sample treatment after the reaction was concentration via an ultrafiltration membrane. Specifically, the reaction solution was filtered through a 0.22 μm filter membrane, and then filtered through an ultrafiltration membrane having a molecular weight cut-off of 100 KDa to collect a retentate. The collected liquid was concentrated on a rotary evaporator and dried in vacuo to yield 293.2 g.

Step (4) was the same as that of Examples 5 and 6. The molecular weight was determined to be 710 KDa before degradation and 75 KDa after degradation. The results are shown in Table 1.

TABLE 1

Polysaccharides extracted from traditional Chinese medicinal materials and their molecular weights before and after degradation

| No. | Name of medicinal material | Weight of medicinal material powder (Kg) | Polysaccharide extracted Weight (Kg) | Polysaccharide extracted Molecular weight (KDa) | After degradation of polysaccharide (400 g) Weight of product (g) | After degradation of polysaccharide (400 g) Yield (%) | After degradation of polysaccharide (400 g) Molecular weight (KDa) |
|---|---|---|---|---|---|---|---|
| 1 | Hericium erinaceus | 5.0 | 0.56 | 650 | 355.2 | 88.8 | 60 |
| 2 | Poria cocos | 5.0 | 0.61 | 740 | 365.2 | 91.3 | 77 |
| 3 | Tremella | 5.0 | 0.72 | 530 | 293.2 | 73.3 | 46 |
| 4 | Lentinus edodes | 5.0 | 0.45 | 880 | 326.0 | 81.5 | 85 |
| 5 | Ganoderma lucidum | 5.0 | 0.50 | >1000 | 274.0 | 68.5 | 22 |
| 6 | Lycium barbarum | 5.0 | 0.75 | 470 | 380.0 | 95.0 | 43 |
| 7 | Astragalus | 5.0 | 0.46 | 710 | 293.2 | 73.3 | 75 |

Example 8

The degradation processes and treatment methods for the following 8 polysaccharides were as follows: 400 g of algin, heparin, heparan sulfate, chondroitin sulfate, dermatan sulfate, hyaluronic acid, chitosan and xanthan gum were respectively weighed and dissolved or swelled in 10 L of water. The pressure for ozone oxidative degradation reaction was set to 0.3 MPa, and the remaining steps were the same as steps (2) of Examples 5 and 6.

After the reaction, each sample was treated as follows. After the degraded reaction solution was filtered through a 0.22 μm ultrafiltration membrane, it was transferred to a membrane concentration device. The membrane concentration steps were as follows: 1) it was initially concentrated with a 100 KDa ultrafiltration membrane, and concentrated until the sample volume was one third of the original volume. Then, the concentration was stopped, and a permeate was collected. 2) The permeate was further concentrated through a membrane having a molecular weight cut-off of 2 KDa. When it was concentrated to one third of the original volume, 3 parts of water was added and the liquid was concentrated again to one third of the original volume. Then, a retentate was collected. 3) The retentate was concentrated on a rotary evaporator, oven-dried in vacuo, pulverized, and weighed.

The methods for measuring the molecular weights of the above eight polysaccharides before and after degradation were the same as those of Examples 1-7. The molecular weights, degradation yields and molecular weights after degradation of algin, heparin, heparan sulfate, chondroitin sulfate, dermatan sulfate, hyaluronic acid, chitosan and xanthan gum are shown in Table 2.

Example 9

The process of preparing polymannuronic acid (PM) and polyguluronic acid (PG) was as follows: 20 L of water was added to 2 Kg of sodium alginate, and heated to allow for fully swelling. Dilute HCl was added to adjust the pH to about 4. After the reaction was conducted at 100° C. for 8 hr, the heating was stopped, and the pH was adjusted to 8.0 by adding a NaOH solution. The insoluble matter was removed by centrifugation, the pH was adjusted to 2.85 by adding dilute HCl, and precipitate A was collected by centrifugation. The supernatant was continuously adjusted to pH 1.0 by adding HCl, and precipitate B was collected by centrifugation. The above precipitate A and precipitate B were respectively dried under reduced pressure, pulverized and weighed. 800 g of polyguluronic acid was obtained from precipitate A, and 600 g of polymannuronic acid was obtained from precipitate B.

Example 10

Step (1): The polymannuronic acid (PM) degradation process was as follows: 400 g of polymannuronic acid powder was weighed, and dissolved in water to a concentration of 20%. The solution was adjusted to pH 5.0, heated to 50° C., and charged with ozone. The ozone oxidative degradation device was the same as in Examples 1-8. The reaction system pressure was set to 0.5 MPa, and the ozone was introduced at a flow rate of 10 g/hr for a total of 2 hr until the reaction was completed.

Step (2): Treatment of degradation product: After the degraded reaction solution was filtered through a 0.22 μm ultrafiltration membrane, it was transferred to a membrane concentration device. The membrane concentration steps were as follows: 1) it was initially concentrated with a 50 KDa ultrafiltration membrane, and concentrated until the sample volume was one third of the original volume. Then, the concentration was stopped, and a permeate was collected. 2) The permeate was further concentrated through a membrane having a molecular weight cut-off of 2 KDa. When it was concentrated to one third of the original volume, 3 parts of water was added and the liquid was concentrated again to one third of the original volume. Then, a retentate was collected. 3) The retentate was concentrated on a rotary evaporator, oven-dried in vacuo, pulverized, and weighed.

Step (3): The molecular weights before and after degradation were determined in the same manner as in Examples 1-8. The experimental results are listed in Table 2.

Example 11

Step (1): Polyguluronic acid (PG) degradation process: 400 g of polyguluronic acid powder was weighed, mixed well with water, and dissolved in NaOH. It was measured to be pH 9.0, and formulated to a concentration of 25%. It was heated to 70° C., and ozone was introduced. The ozone oxidative degradation device and setting were the same as in Example 10. The ozone was introduced at a flow rate of 10 g/hr for a total of 2 hr until the reaction was completed.

Step (2): The degradation product was treated in the same manner as in Example 10.

Step (3): The molecular weights before and after degradation were measured in the same manner as in Example 10. The experimental results are listed in Table 2.

Example 12

The process of preparing sulfated polymannuronic acid (S-PM) was as follows: 200 g of polymannuronic acid was weighed and 2 L of pyridine was added. The mixture was stirred to give a homogenous suspension. The suspension was condensed to about 0° C., and 500 mL of pre-cooled chlorosulfonic acid-pyridine solution (containing 300 g of chlorosulfonic acid) was added slowly. After the addition was completed, stirring was continued for 3 hr until the reaction was completed. After the mixture was set aside for a period of time, the solvent was filtered off, and the solid was washed with 5 L of 95% ethanol to remove the residual pyridine solvent. After the ethanol was filtered off, 5 L of water was added to dissolve the solid matter, NaOH was added to adjust the pH to about 12, and the bound pyridine was allowed to completely volatilize. A precipitate was obtained by adding 5 L of ethanol, centrifuged, oven-dried, pulverized and weighed, to obtain 230 g of a solid powder. The molecular weight was measured to be 5 KDa.

Example 13

Sulfated polyguluronic acid (S-PG) was prepared in the same manner as in Example 12. 240 g of a solid powder with a molecular weight of 8 KDa was obtained.

Example 14

The sulfated polymannuronic acid (S-PM) degradation process was as follows: 200 g of polymannuronic acid powder was weighed, and dissolved in water to a concentration of 30%. The solution was adjusted to pH 7.0, heated to 50° C., and charged with ozone. The ozone oxidative degradation device and setting were the same as in Example 10. The ozone was introduced at a flow rate of 10 g/hr for a total of 3 hr until the reaction was completed.

The degradation product treatment and molecular weight measurement were the same as in Example 10. The sulfate contents before and after degradation were both 40%. For the measurement method, please see the method used in "Determination of sulfate content" as disclosed hereinabove. Other experimental results are listed in Table 2.

Example 15

The degradation process, degradation product treatment and molecular weight measurement for sulfated polyguluronic acid (S-PG) were the same as in Example 14. The sulfate contents before and after degradation were both 38%. Other experimental results are listed in Table 2.

TABLE 2

Molecular weights before and after degradation and yields of the commercially available and home-made polysaccharides

| No. | Polysaccharide name | Molecular weight before degradation (KDa) | Molecular weight after degradation (KDa) | Yield (%) |
|---|---|---|---|---|
| 1 | algin | 100 | 10 | 86 |
| 2 | heparin | 15 | 8 | 88 |
| 3 | heparan sulfate | 22 | 10 | 77 |
| 4 | chondroitin sulfate | 50 | 5 | 79 |
| 5 | dermatan sulfate | 80 | 6 | 83 |
| 6 | hyaluronic acid | >100 | 50 | 78 |
| 7 | chitosan | 80 | 20 | 95 |
| 8 | xanthan gum | >100 | 20 | 75 |
| 9 | polymannuronic acid (PM) | 4 | 1 | 74 |
| 10 | polyguluronic acid (PG) | 6 | 3 | 76 |
| 11 | Sulfated polymannuronic acid (S-PM) | 5 | 1.5 | 82 |
| 12 | Sulfated polyguluronic acid (S-PG) | 8 | 4 | 91 |

Example 16

This Example compared and investigated the effects of catalysts on the degradation rate of algin using ozone oxidative degradation of algin as a model. The method was as follows.

Step (1): 9 portions of algin of equal mass, 200 g per portion, were weighed, dissolved in 20 L of water, respectively, and heated to promote dissolution. After dissolution, catalysts were introduced when the temperature was stabilized at 40° C. Except the first portion, the catalytic conditions of the remaining 8 portions of reaction solutions were: 1 mM $FeCl_3$, 1 mM $NiSO_4$, 1 mM $CoCl_3$, 1 mM $MnO_2$, 10 mM $H_2O_2$, light illumination provided by a 20 W high efficiency ultraviolet lamp, 10 g of activated carbon fine powder, and 5 g of NaOH.

Step (2): Reaction conditions and sampling during the reaction. The ozone flow rate was the same as in Example 1. The pressure was set to normal pressure, i.e., 0.1 MPa. The reaction was started by introducing ozone, and was sampled every 10 min to measure the molecular weight.

Figure 1:
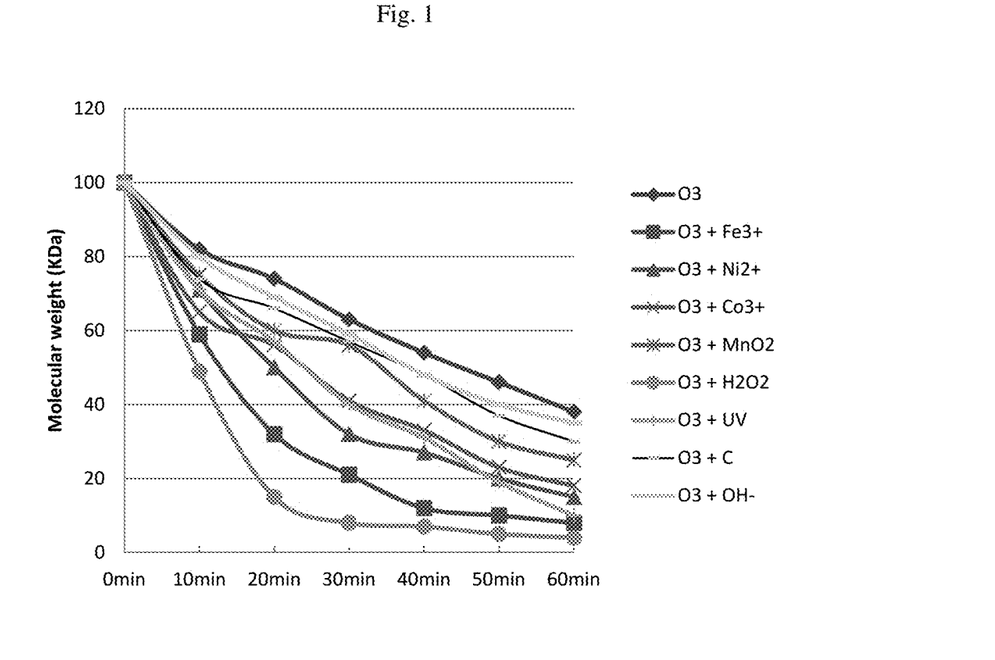
FIG. 1 is a graph showing the effects of catalysts on the degradation rate of a polysaccharide.

Step (3): Molecular weight measurement: The molecular weight of the starting material of the reaction, algin, was the molecular weight at 0 min. The sample solutions taken at the other time points were dialyzed in a dialysis bag having a molecular weight cut-off of 10 KDa for 12 hr to remove salts, metal ions and reacted small molecule fragments. The dialyzed sample was filtered through a 0.22 μm filter membrane to obtain a test sample. The measurement method was the same as in Example 1. FIG. 1 is a graph showing the change in molecular weight of a polysaccharide over time under the above reaction conditions. As can be seen from FIG. 1, the selected catalysts can significantly accelerate degradation of the polysaccharide.

Example 17

Step 1): Preparation of a Mannuronic Diacid Oligosaccharide Product

Polymannuronic acid (PM) was prepared as described in Example 9. The specific operations are briefly described as below: 5 Kg of sodium alginate was formulated into a ~10% solution, and the pH was adjusted to about 3.0 by adding dilute hydrochloric acid. The solution was heated to 80° C., and stirred. It was allowed to be reacted for 10 hr before the heating was stopped. After cooling to room temperature, the pH was adjusted to 9.0 by adding NaOH, and further adjusted to 2.85 by adding dilute hydrochloric acid. The solution was centrifuged at 5000 rpm for 10 min. The supernatant was collected, and adjusted to pH 1.0 by adding HCl. After centrifugation, the precipitate was collected, concentrated on a rotary evaporator, and dry in vacuo to give 1,500 g of an M-segment intermediate. 500 g of the M-segment intermediate was weighed, and dissolved in distilled water to prepare a solution in a volume of 5 L. The solution was adjusted to pH 6.5 with NaOH, and heated in a water bath to control the reaction temperature to be 75° C. The outlet pressure of an oxygen cylinder was adjusted, and when the system pressure was stable at 0.1 MPa, the gas flow rate at the gas outlet and the power of an ozone generator were adjusted, such that ozone was introduced into the reaction solution at a mass concentration flow rate of 8 g/hr. After 4 hr of reaction, the introduction of ozone was stopped, and a suitable amount of water was added to adjust the concentration of the solution to about 10%. The solution was filtered through an ultrafiltration membrane with a molecular weight cut-off of 2,000 Da to collect a retentate. The collected liquid was concentrated on a rotary evaporator and dried under vacuum to obtain 350 g of mannuronic diacid product A.

Step 2) Evaluation of Pharmacological Activity

1. Protective Effect of Product A on Aβ-Induced Nerve Cell Injury

The test was conducted according to the "model for evaluating cell viability", and the experimental procedure was as follows: SH-SY5Y cells (neuroblastoma cells) were seeded in a 96-well plate (3000 cells/well). After 24 hr, the medium was removed, and for the dosing groups, 10 μL per well of a drug (10 mg/mL) was added for pretreatment for 0.5 hr (formulated in a serum-free culture medium; 3 replicates per dose). Then, aggregated Aβ 1-42 (Aβ1-42 was formulated in a PBS solution to 1 mg/ml, and incubated in an incubator at 4° C. for 24 hr to form an aggregated state, at a final concentration of 2 μM) was added and incubated for 48 hr. The cell viability was detected by CCK8.

Figure 2:
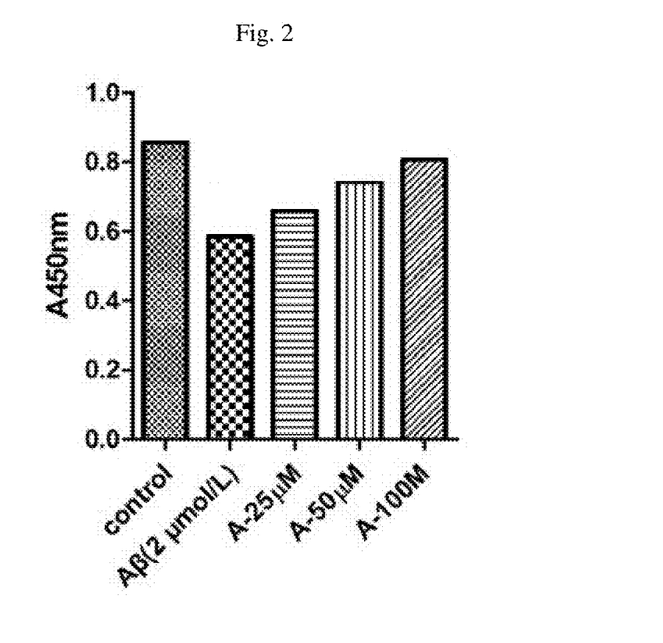
FIG. 2 shows a protective effect of the ozone degradation product of a polysaccharide on nerve cells.

The results showed that 48-hour treatment of SH-SY5Y cells with 2 μM Aβ1-42 could induce significant cell damage and decreased cell viability, while 25, 50 and 100 μg/mL product A could significantly inhibit Aβ-induced decrease in cell viability; see FIG. 2. The above results indicate that product A can protect nerve cells from the toxic effects of Aβ at a low concentration (25 μg/mL), a medium concentration (50 μg/mL), and a high concentration (100 μg/mL).

What is claimed is:

1. A method of controllable degradation of a water-soluble polysaccharide, the method comprising:
    contacting an aqueous solution of the water-soluble polysaccharide with an amount of ozone, such that a sugar chain of the water-soluble polysaccharide is subjected to an oxidative degradation reaction to give an aqueous solution containing a degraded water-soluble polysaccharide/oligosaccharide having a lower molecular weight than the water-soluble polysaccharide,
    wherein:
    the water-soluble polysaccharide is a sulfated polyguluronic acid; and
    the oxidative degradation reaction is carried out in a pressurized reactor at a pressure from greater than 0.1 MPa to 1.0MPa.

2. The method according to claim 1, wherein the amount of the ozone consumed in the oxidative degradation reaction is controlled to produce a degraded water-soluble polysaccharide/oligosaccharide having a target molecular weight.

3. The method of claim 2, wherein the amount of ozone consumed in the oxidative degradation reaction is controlled by controlling the flow rate and introduction time of the ozone.

4. The method of claim 1, wherein the water-soluble polysaccharide is in a 1-40% aqueous solution.

5. The method of claim 1, wherein the reaction time of the oxidative degradation reaction does not exceed 4 hours.

6. The method of claim 1, wherein the oxidative degradation reaction is carried out at a temperature of 20-60° C.

7. The method of claim 1, further comprising:
  prior to contacting the aqueous solution with ozone, adjusting the pH of the aqueous solution of the water-soluble polysaccharide to 3-10 to promote dissolution of the water-soluble polysaccharide.

8. The method of claim 1, wherein the amount of ozone consumed in the oxidative degradation reaction is 10-500 mg per gram of the water-soluble polysaccharide.

9. The method of claim 1, wherein the oxidative degradation reaction is carried out in the absence of a catalyst.

10. The method of claim 1, wherein:
  the oxidative degradation reaction is carried out in the presence of a catalyst; and
  the reaction time of the oxidative degradation does not exceed 2 hours.

11. The method of claim 10, wherein the catalyst is one or more of a base, a metal ion, hydrogen peroxide, ultraviolet light and activated carbon.

12. The method of claim 11, wherein the base is a sodium or potassium hydroxide, a sodium or potassium carbonate, or a sodium or potassium phosphate.

13. The method of claim 11, wherein the metal ion is iron ion, nickel ion, cobalt ion, or manganese ion.

14. The method of claim 1, further comprising,
  adding ethanol to the aqueous solution of the degraded water-soluble polysaccharide/oligosaccharide, at a volume concentration (V/V) of 10-90%, in order to precipitate the degraded water-soluble polysaccharide/oligosaccharide.

15. The method of claim 1, further comprising,
  concentrating the aqueous solution of the degraded water-soluble polysaccharide/oligosaccharide with an ultrafiltration membrane,
  wherein the ultrafiltration membrane has a molecular weight cut-off in the range of from 1 to 100 KDa.

16. The method of claim 1, wherein the oxidative degradation reaction forms the degraded water-soluble polysaccharide/oligosaccharide with a yield of greater than 90%.

17. The method of claim 1, wherein the oxidative degradation reaction is carried out in a pressurized reactor at a pressure from 0.3 MPa to 1.0 MPa.

18. The method of claim 1, wherein the oxidative degradation reaction is carried out in a pressurized reactor at a pressure from 0.5 MPa to 1.0 MPa.

* * * * *